US012361668B2

(12) United States Patent
Kim et al.

(10) Patent No.: US 12,361,668 B2
(45) Date of Patent: Jul. 15, 2025

(54) METHOD AND APPARATUS FOR MEASURING MOTILITY OF CILIATED CELLS IN RESPIRATORY TRACT

(71) Applicant: CHUNG ANG UNIVERSITY INDUSTRY ACADEMIC COOPERATION FOUNDATION, Seoul (KR)

(72) Inventors: Jun Ki Kim, Seoul (KR); Woo June Choi, Seoul (KR)

(73) Assignee: CHUNG ANG UNIVERSITY INDUSTRY ACADEMIC COOPERATION FOUNDATION, Seoul (KR)

(*) Notice: Subject to any disclaimer, the term of this patent is extended or adjusted under 35 U.S.C. 154(b) by 388 days.

(21) Appl. No.: 17/811,769

(22) Filed: Jul. 11, 2022

(65) Prior Publication Data

US 2023/0052716 A1  Feb. 16, 2023

(30) Foreign Application Priority Data

Aug. 11, 2021 (KR) .......................... 10-2021-0105944

(51) Int. Cl.
*G06V 10/25* (2022.01)
*G06T 7/00* (2017.01)
(Continued)

(52) U.S. Cl.
CPC ............ *G06V 10/25* (2022.01); *G06T 7/0014* (2013.01); *G06T 7/11* (2017.01); *G06V 10/761* (2022.01);
(Continued)

(58) Field of Classification Search
CPC ...... G06V 10/25; G06V 10/761; G06V 20/69; G06V 10/42; G06V 10/987; G06V 20/695;
(Continued)

(56) References Cited

U.S. PATENT DOCUMENTS

| 2014/0118529 A1* | 5/2014 | Zheng .................. G02B 21/365 348/80 |
| 2015/0310254 A1* | 10/2015 | Chennubhotla ......... G06T 7/269 382/133 |
| 2020/0245905 A1* | 8/2020 | Chen .................. A61B 1/00177 |

FOREIGN PATENT DOCUMENTS

| KR | 10-1999-0039172 A | 6/1999 |
| KR | 10-2004-0044719 A | 5/2004 |

(Continued)

OTHER PUBLICATIONS

Jing, Joseph C. et al, "Visualization and Detection of Ciliary Beating Pattern and Frequency in the Upper Airway using Phase Resolved Doppler Optical Coherence Tomography", Aug. 17, 2017 [retrieved on Sep. 18, 2024], Scientific Reports [online], 7:8522. Retrieved from National Library of Medicine: <URL: https://www.ncbi.nlm.nih.gov/pmc/articles/PMC5561030/>. <DOI: 10.1038/s41598-017-08968-x>. (Year: 2017).*

(Continued)

*Primary Examiner* — Matthew C Bella
*Assistant Examiner* — Nicholas John Helco
(74) *Attorney, Agent, or Firm* — Studebaker Brackett PLLC

(57) ABSTRACT

The present disclosure relates to a method and an apparatus for measuring motility of ciliated cells in a respiratory tract. The method includes the operations of: acquiring image data including a plurality of frames of respiratory tract organoids; identifying positions of ciliated cells by performing motion-contrast imaging on the image data; when a region of interest
(Continued)

(ROI) related to the position of the ciliated cells is selected, measuring a ciliary beat frequency (CBF) related to motility of cilia included in the selected region of interest using cross-correlation between the plurality of frames; and expressing the cilia included in the region of interest in a preset display method on the basis of the range of the measured ciliary beat frequency.

12 Claims, 6 Drawing Sheets

(51) Int. Cl.
  *G06T 7/11* (2017.01)
  *G06V 10/74* (2022.01)
(52) U.S. Cl.
  CPC .............. *G06F 2218/10* (2023.01); *G06T 2207/10056* (2013.01); *G06T 2207/30024* (2013.01)
(58) Field of Classification Search
  CPC ............ G06T 7/0014; G06T 7/11; G06T 2207/10056; G06T 2207/30024; G06T 7/0016; G06T 7/0012; G06T 7/20; G06T 2207/10061; G06T 2207/10068; G06T 2207/20012; G06T 2207/20021; G06T 2207/20056; G06T 7/215; G06T 7/262; G06T 2207/10148; G06F 2218/10; A61B 1/00009; A61B 1/267; A61B 1/000095; A61B 5/0033; A61B 5/0084; A61B 5/08; A61B 5/1107; A61B 5/1128; A61B 5/7257; A61B 2576/00; A61B 5/087; A61B 5/7278; A61B 5/7282; G02B 21/008; A61H 2230/42
  See application file for complete search history.

(56) References Cited

FOREIGN PATENT DOCUMENTS

| KR | 100517120 B1 * | 9/2005 | ... G06T 2207/10016 |
|---|---|---|---|
| KR | 10-1582735 B1 | 1/2016 | |
| KR | 10-2021-0041046 A | 4/2021 | |
| WO | WO-2018217882 A1 * | 11/2018 | ........ B01L 3/502769 |

OTHER PUBLICATIONS

Li et al, "Methods to measure and analyze ciliary beat activity: Ca2+ influx-mediated cilia mechanosensitivity", Oct. 5, 2012 [retrieved on Sep. 19, 2024], Pflügers Archiv—European Journal of Physiology [online], vol. 464, pp. 671-680. Retrieved from Springer Link: <URL: https://link.springer.com/article/10.1007/s00424-012-1164-1>.<DOI: https://doi.org/10.1007/s00424-012-1164-1>. (Year: 2012).*
An Office Action mailed by the Korean Intellectual Property Office on Jan. 31, 2023, which corresponds to Korean Patent Application No. 10-2021-0105944 and is related to U.S. Appl. No. 17/811,769.

* cited by examiner

METHOD AND APPARATUS FOR MEASURING MOTILITY OF CILIATED CELLS IN RESPIRATORY TRACT

CROSS-REFERENCE TO RELATED APPLICATION

The present application is based upon and claims the benefit of priority to Korean Patent Application No. 10-2021-0105944, filed on Aug. 11, 2021. The disclosure of the above-listed application is hereby incorporated by reference herein in its entirety.

BACKGROUND

1. Technical Field

The present disclosure relates to a method and an apparatus for measuring motility of ciliated cells in a respiratory tract.

2. Description of Related Art

One of the major functions of the airway epithelium is mucociliary clearance for discharging foreign substances, such as dust, bacteria, and co-toxic substances entering during inhalation, out of the airway through a mucociliary motion. This is an important primary defense mechanism of the respiratory tract.

If there is a birth defect or an acquired defect in such ciliary motion, foreign substance transfer efficiency is lowered, and may result in inflammatory respiratory diseases, etc. Therefore, it is important to selectively evaluate the activity of ciliary epithelial cells in order to quickly determine airway health conditions and lung function states.

Since a general ciliary motion is similar to a pendulum motion, a ciliary beat frequency (CBF), which is the number of oscillations per second, can be measured, thereby evaluating the activity of cilia.

A method for measuring a ciliary beat frequency (CBF) which has, to date, been the most commonly used, is high-speed digital camera image analysis. In high-speed digital camera image analysis, after a video image of moving cilia is recorded, a fast Fourier transform (FFT) is applied to a signal strength profile for each pixel of the video image to measure a frequency distribution of a time-varying signal, and then, the highest frequency is used to evaluate the ciliary beat frequency (CBF) by the ciliary motion.

However, in the case of the respiratory tract, since ciliated cells are collected at high density in one ciliated epithelium and motion paths of the ciliated cells can be overlapped with motion paths of neighboring ciliated cells, when a single pixel-based FFT is used, a number of high frequencies may be generated. Accordingly, there may be a problem in that frequency analysis becomes obscure and it may be difficult to actually determine a ciliary beat frequency.

Furthermore, since ciliated cells in the respiratory tract are vertically arranged on the epithelial mucosa in the form of thin hairs of 5 to 7 µm, the intensity of the scattered light signal by the ciliated cells is weaker than that of the surrounding epithelial tissues. Therefore, since it is very difficult to determine the form or location of cilia from an image of a general reflective microscopic camera or a transmission microscopic camera with the naked eye, at the time of CBF measurement of target ciliated cells, a region of interest (ROI) may be set by subjective judgment of a user, and this may cause a considerable error in CBF measurement.

SUMMARY

The present disclosure has been made to solve the above-mentioned problems occurring in the prior art, and in an aspect of the present disclosure, it is an object to provide a method and an apparatus for measuring motility of ciliated cells in a respiratory tract.

The aspects of the present disclosure are not limited to those mentioned above, and other aspects not mentioned herein will be clearly understood by those skilled in the art from the following description.

To accomplish the above objects, in an aspect of the present disclosure, there is provided a method for measuring motility of ciliated cells in a respiratory tract including the operations of: acquiring image data, including a plurality of frames of respiratory tract organoids; identifying positions of ciliated cells by performing motion-contrast imaging on the image data; when a region of interest (ROI) related to the position of the ciliated cells is selected, measuring a ciliary beat frequency (CBF) related to motility of cilia included in the selected region of interest using cross-correlation between the plurality of frames; and expressing the cilia included in the region of interest in a preset display method on the basis of a range of the measured ciliary beat frequency, wherein the ciliary beat frequency measuring operation is to measure the ciliary beat frequency by digitizing image similarity between a reference frame among the plurality of frames and the remaining frames into a correlation coefficient.

In the present disclosure, the position identifying operation may extract a dynamic signal component according to the motion of the ciliary cells among data components included in the image data to identify the position of the ciliated cells.

In the present disclosure, if there are a plurality of regions of interest, in the ciliary beat frequency measuring operation, a ciliary beat frequency for each of the plurality of regions of interest is measured. In the operation of expressing in the predetermined display method, each of the plurality of regions of interest is displayed in a color corresponding to the range of each measured ciliary beat frequency.

In the present disclosure, the correlation coefficient has a waveform vibrating at a predetermined period.

In the present disclosure, the ciliary beat frequency measuring operation is to calculate the number of peaks of the waveform in the ciliary beat frequency.

In the present disclosure, even when the focus of the microscope is moved in the depth direction, the ciliary beat frequencies measured in the ciliary beat frequency measuring operation are the same.

In another aspect of the present disclosure, there is provided an apparatus for measuring motility of ciliated cells in a respiratory tract including: a communication unit; a memory storing at least one process for measuring motility of ciliated cells in a respiratory tract; and a processor operating according to the process. The processor, based on the process, is configured to: acquire image data including a plurality of frames of respiratory tract organoids; identify positions of ciliated cells by performing motion-contrast imaging on the image data; when a region of interest (ROI) related to the position of the ciliated cells is selected, measure a ciliary beat frequency (CBF) related to motility of cilia included in the selected region of interest using cross-correlation between the plurality of frames; and express the cilia included in the region of interest in a preset display method on the basis of the range of the measured ciliary beat frequency. The processor measures the ciliary beat frequency by digitizing image similarity between a reference frame among the plurality of frames and the remaining frames into a correlation coefficient.

In the present disclosure, when identifying the position of the ciliated cells, the processor extracts a dynamic signal component according to the motion of the ciliary cells among data components included in the image data to identify the position of the ciliated cells.

In the present disclosure, if there are a plurality of regions of interest, when measuring the ciliary beat frequency, the processor measures a ciliary beat frequency for each of the plurality of regions of interest. When expressing in the predetermined display method, the processor displays each of the plurality of regions of interest in a color corresponding to the range of each measured ciliary beat frequency.

In the present disclosure, the correlation coefficient has a waveform vibrating at a predetermined period.

In the present disclosure, when measuring the ciliary beat frequency, the processor calculates the number of peaks of the waveform in the ciliary beat frequency.

In the present disclosure, the processor measures the same ciliary beat frequencies even when the focus of the microscope is moved in the depth direction.

In addition to the above, other methods and systems for embodying the present disclosure and a computer readable recording medium to record computer programs for executing the method may be additionally provided.

DETAILED DESCRIPTION

Figure 1:
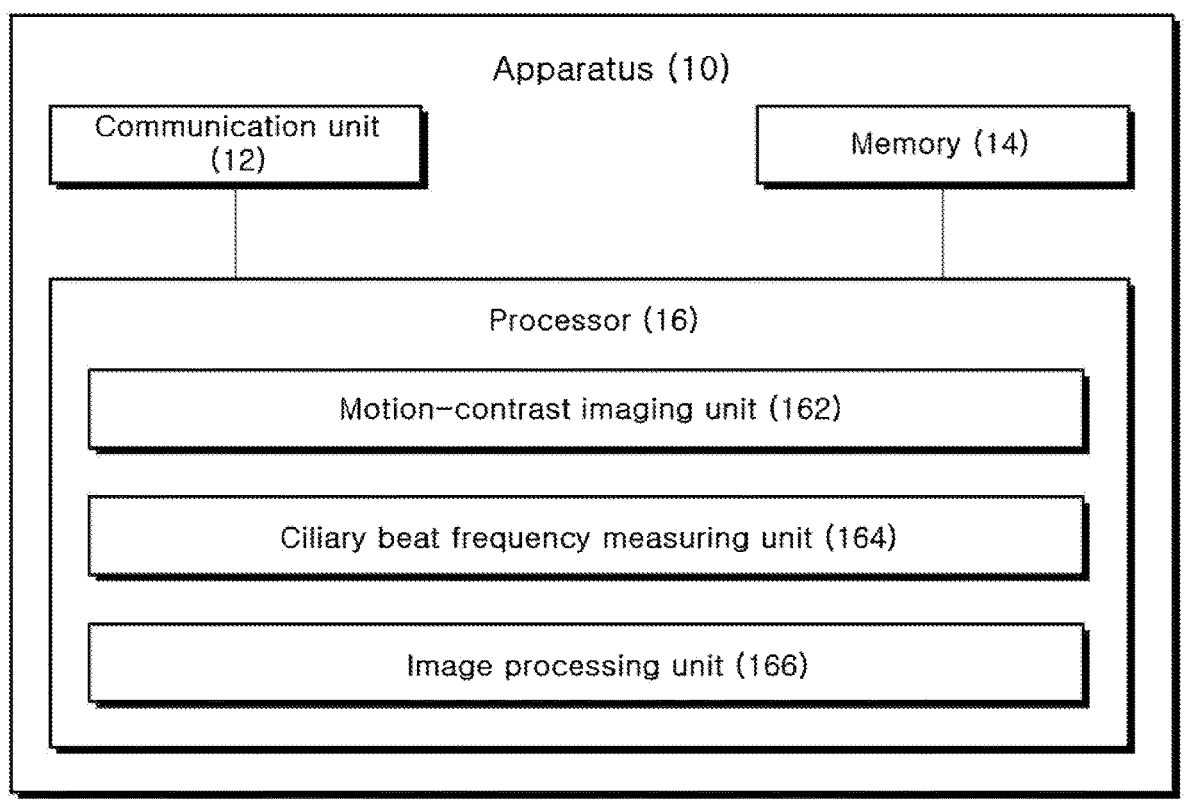
FIG. 1 is a schematic block diagram of an apparatus for measuring motility of ciliated cells in a respiratory tract according to the present disclosure.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skill in the art could fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components in addition to components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Terms, such as "below," "beneath," "lower," "above," "upper," and the like, which have spatially relative concepts, may be used to facilitate correlation between one component and other components, as illustrated in the drawings. Such spatially relative terms should be understood as terms including different directions of components during use or operation, in addition to the direction illustrated in the drawings. For example, if the components illustrated in the drawings are turned upside down, the components described as "below" or "beneath" may be placed "above" of other components. Thus, the exemplary term "under" may include all of the directions, "below" and "above". The components may be oriented in other directions, so that the spatially relative terms can be interpreted according to the orientation.

Hereinafter, preferred embodiments of the present disclosure will be described in detail with reference to the accompanying drawings.

The meaning of the terms used in the present disclosure will be briefly described with reference to the description. It should be noted, however, that the description of the terms is intended to assist in the understanding of the present disclosure, and is not intended to limit the technical spirit of the present disclosure if not explicitly disclosed in limiting the present disclosure.

In the present specification, an "apparatus" includes all of a variety of devices capable of providing a result to a user by performing operation processing. For example, an apparatus may be in the form of a computer and a mobile terminal capable of wired and wireless communication. The computer may be in the form of a server that receives a request from a client and performs information processing. In addition, the computer may be a sequencing device for performing sequencing. The mobile terminal may be one among a mobile phone, a smart phone, a personal digital assistant (PDA), a portable multimedia player (PMP), a navigation, a notebook PC, a slate PC, a tablet PC, an ultrabook, a wearable device, for example, a watch-type terminal such as a smartwatch, a glasses-type terminal such as smart glasses, a head mounted display (HMD), and the like.

FIG. 1 is a schematic block diagram of an apparatus for measuring motility of ciliated cells in a respiratory tract according to the present disclosure.

Figure 2:
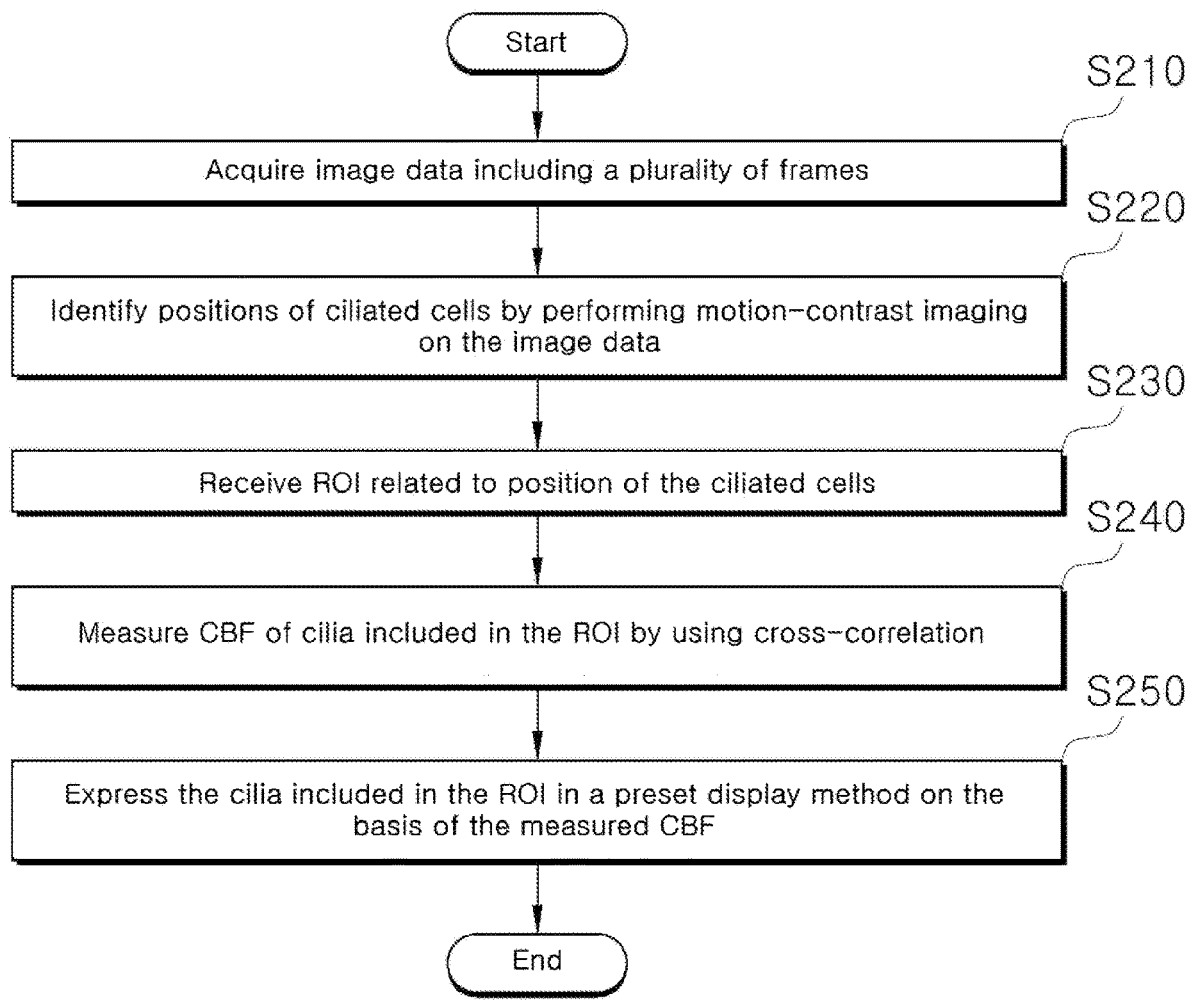
FIG. 2 is a flow chart of a method for measuring motility of ciliated cells in a respiratory tract according to the present disclosure.

FIG. 2 is a flow chart of a method for measuring motility of ciliated cells in a respiratory tract according to the present disclosure.

Figure 3:
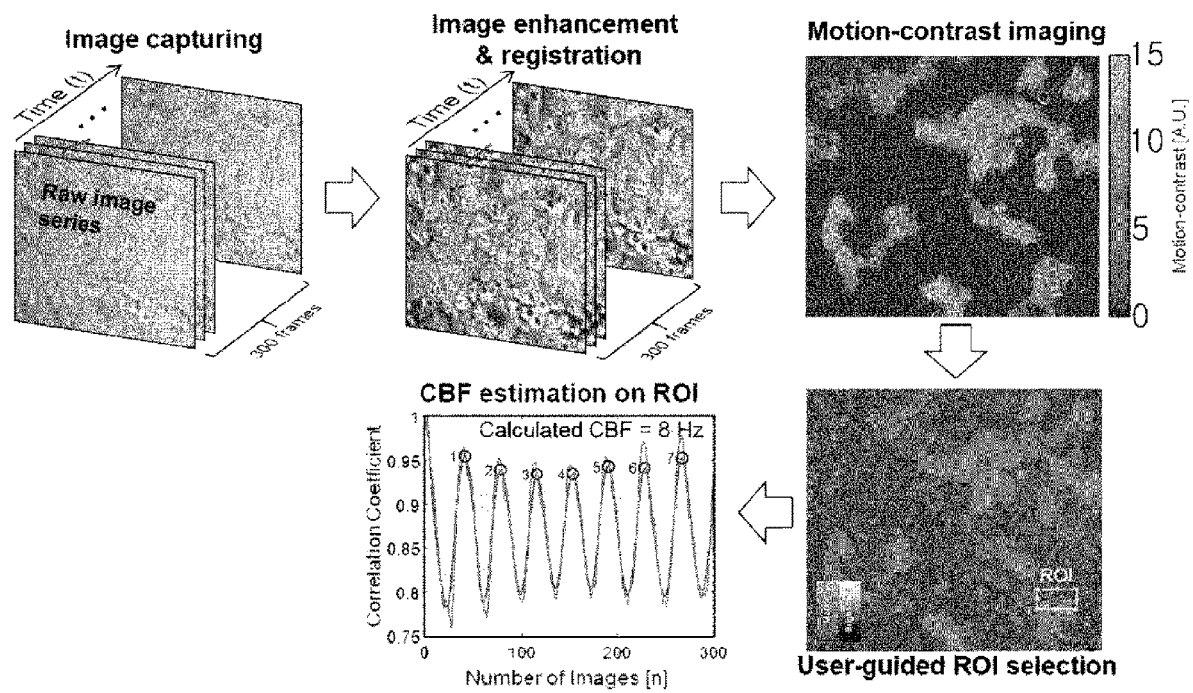
FIG. 3 is a view illustrating an overall process for measuring motility of ciliated cells in a respiratory tract according to the present disclosure.

FIG. 3 is a view illustrating an overall process for measuring motility of ciliated cells in a respiratory tract according to the present disclosure.

Figure 4:
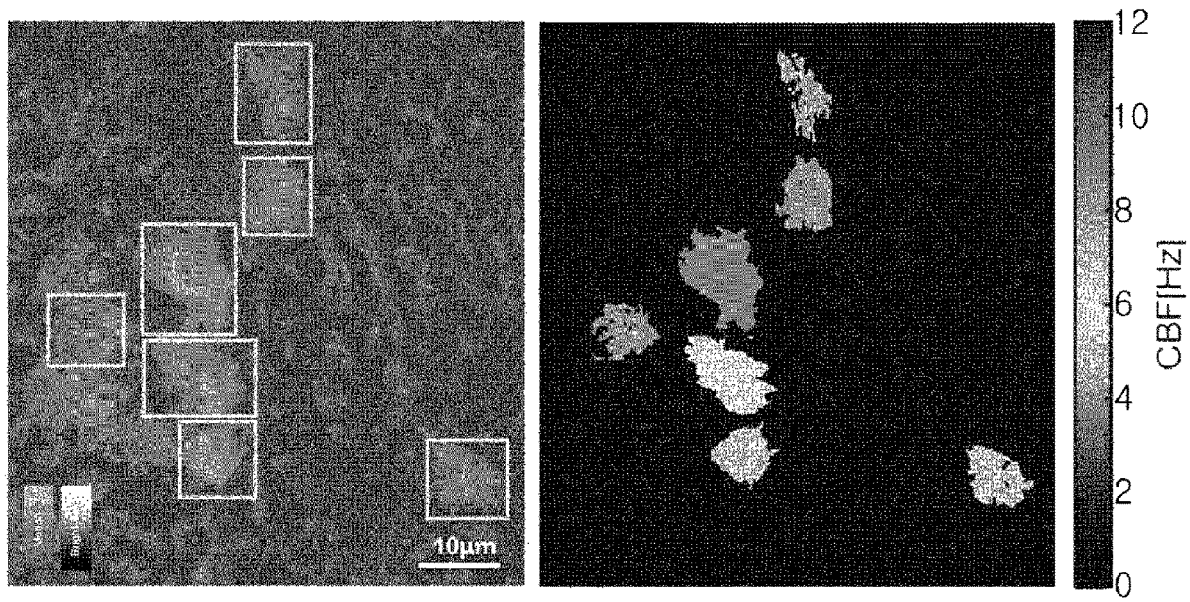
FIG. 4 is a view illustrating a plurality of regions of interest according to the present disclosure.

FIG. 4 is a view illustrating a plurality of regions of interest according to the present disclosure.

Figure 5:
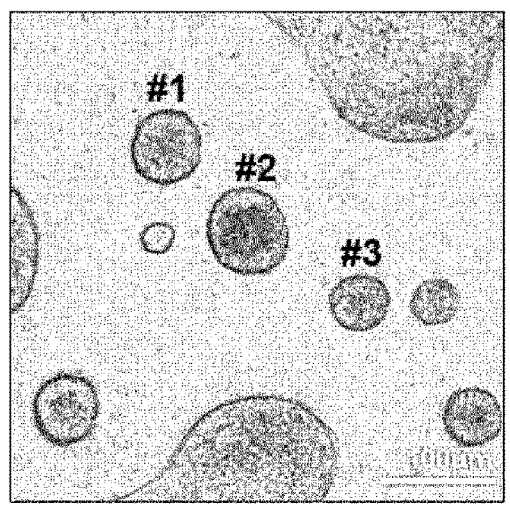
FIG. 5 is a view illustrating a case in which a plurality of organoids in a microscope according to the present disclosure is observed.
Figure 5:
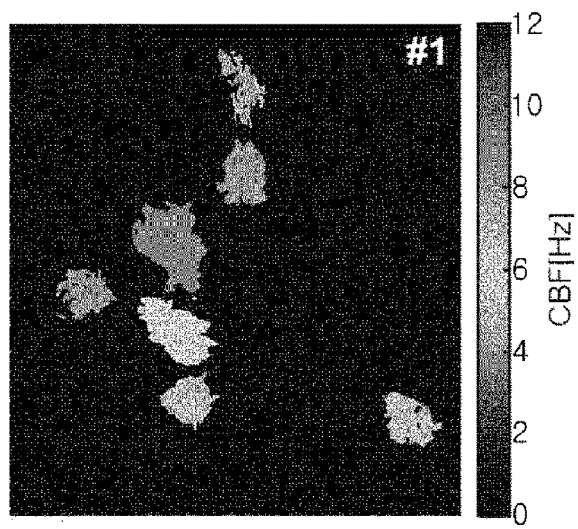
Figure 5:
Figure 5:
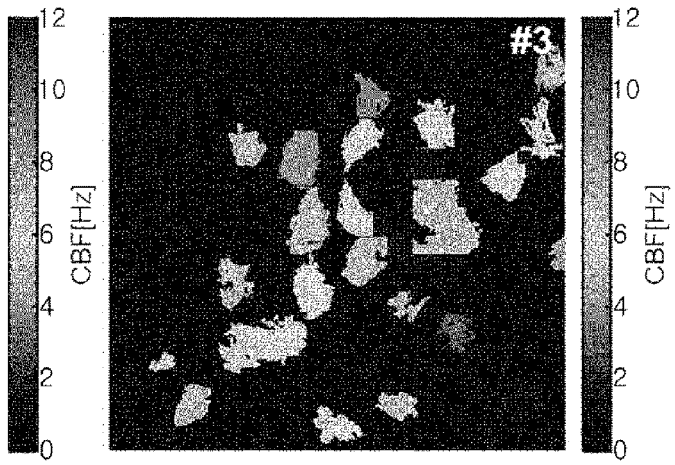

FIG. 5 is a view illustrating a case in which a plurality of organoids in a microscope according to the present disclosure is observed.

Figure 6A:
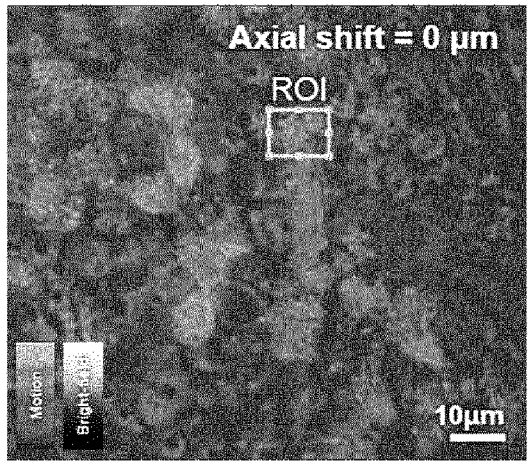
FIGS. 6A and 6B are views illustrating the measurement of the ciliated beat frequency when a focus movement of the microscope is generated according to the present disclosure.
Figure 6A:
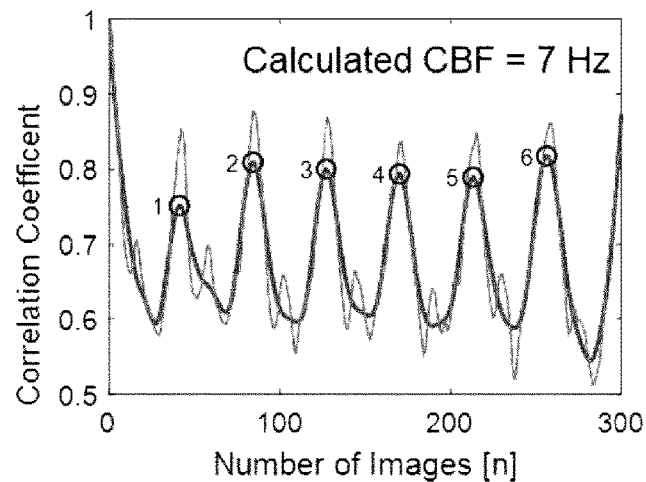
Figure 6B:
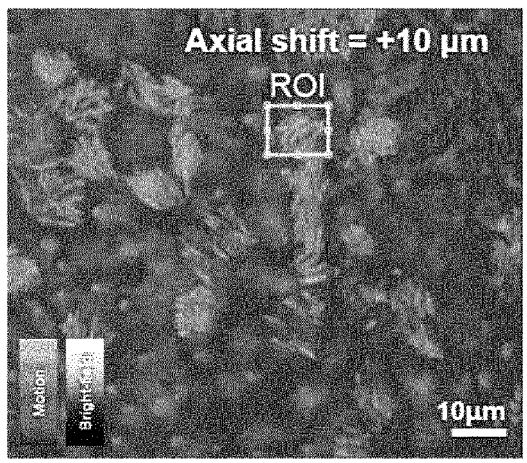
Figure 6B:
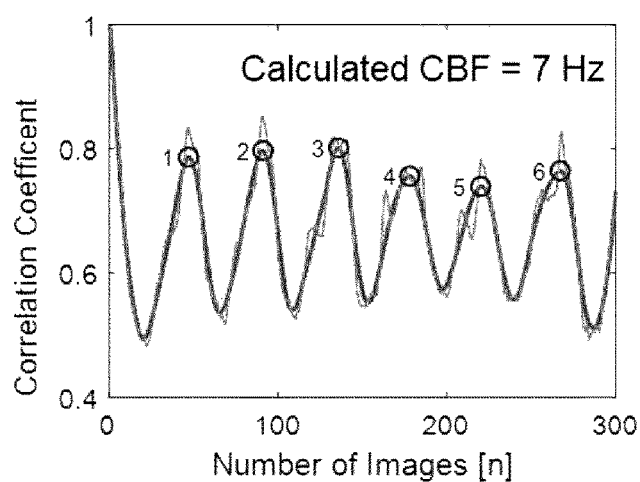

FIGS. 6A and 6B are views illustrating the measurement of a ciliated beat frequency when a focus movement of the microscope is generated according to the present disclosure.

With reference to FIG. 1, an apparatus 10 for measuring motility of ciliated cells in the respiratory tract, hereinafter, referred to as an apparatus, according to the present disclosure will be described.

The apparatus 10 according to the present disclosure obtains image data of respiratory tract organoids from an external apparatus 10 (not shown) and analyzes the acquired image data to measure motility of ciliated cells in the respiratory tract.

Here, the image data may include a plurality of frames. For example, the image data may include 300 frames. In this instance, when the number of frames per second of the image data is 300 fps (frames per second), the image data can be data of one second length.

Here, the external device (not shown) may be a microscope. That is, when a user observes organoids in the respiratory tract for a predetermined period of time through the microscope, image data of the organoids observed for the predetermined period of time, for instance, one second, can be provided to the apparatus 10.

The apparatus 10 can capture images with the number of frames, for instance, 300 frames, based on the number of frames per second, for instance, 300 fps, from the obtained image data for the predetermined period of time, for instance, one second.

The apparatus 10 performs motion-contrast imaging with respect to image data including a plurality of frames to identify an accurate position of the ciliated cells, and provides data of which the corresponding position is identified to a user to allow the user to more objectively set a region of interest (ROI).

When receiving the region of interest (ROI) from the user, the apparatus 10 can measure a ciliary beat frequency (CBF) included in the region of interest (ROI) using cross-correlation between the frames only for the region of interest selected from the entire area of the frames.

The apparatus 10 can express the cilia in the region of interest according to the measured ciliary beat frequency to provide the same to the user.

The apparatus 10 can include all of various devices capable of providing a result to a user by performing calculation processing.

Here, the apparatus 10 can be in the form of a computer. More specifically, the computer can include all of various devices capable of providing a result to a user by performing operation processing.

For example, the computer may be one among a desktop PC, a notebook computer, a smartphone, a tablet PC, a cellular phone, a PCS phone, a PC phone, a palm PC, a personal digital assistant (PDA), or the like. In addition, if the smart glasses or the head mounted display (HMD) device includes a computing function, an augmented reality and virtual reality implementation device can be a computer.

The apparatus 10 may include a communication unit 12, a memory 14, and a processor 16. The processor 16 may include a motion-contrast imaging unit 162, a ciliary beat frequency measuring unit 164, and an image processing unit 166. Here, the apparatus 10 may include fewer components or more components than the components illustrated in FIG. 1.

The communication unit 12 may include one or more modules enabling wireless communication between the apparatus 10 and an external device (not shown), between the apparatus 10 and an external server (not shown), or between the apparatus 10 and a communication network (not shown).

Here, the communication network (not shown) can transmit and receive various types of information between the apparatus 10, an external device (not shown), and an external server (not shown). The communication network (not shown) can use various types of communication networks, for instance, wireless communication methods, such as a wireless local area network (WLAN), Wi-Fi, Wibro, WiMAX, high speed downlink packet division access (HSDPA), and the like, or wired communication methods, such as Ethernet, xDSL (ADSL or VDSL), hybrid fiber coax (HFC), fiber to the curb (FTTC), fiber to the home (FTTH), and the like.

On the other hand, the communication network (not shown) is not limited to the communication methods set forth above, and can include all types of communication methods which have been widely known or will be later developed in addition to the above.

The communication unit 12 may include one or more modules connecting the apparatus 10 to one or more networks.

The memory 14 can store data that supports various functions of the apparatus 10. The memory 14 can store a number of application programs (application programs or applications) driven in the apparatus 10, at least one process, data, and commands for operation of the apparatus 10. At least some of these application programs may exist for the basic functions of the apparatus 10. On the other hand, the application programs can be stored in the memory 14 and installed on the apparatus 10 to perform the operations or functions of the apparatus 10 by the processor 16.

In addition to the operations associated with the application programs, the processor 16 is typically capable of controlling the overall operation of the apparatus 10. The processor 16 can processing input or output signals, data, information, etc. through the components described above or operates the application programs stored in the memory 14 so as to provide or process appropriate information or functions to the user.

In addition, the processor 16 can control at least some of the components described with reference to FIG. 1 to operate the application programs stored in the memory 14. Furthermore, the processor 16 can combine and operate at least two of the components included in the apparatus 10 with each other in order to operate the application programs.

In addition, the motion-contrast imaging unit 162, the ciliary beat frequency measuring unit 164, and the image processing unit 166 included in the processor 16 can perform their own functions as described above. The motion-contrast imaging unit 162 can perform motion-contrast imaging on the image data. The ciliary beat frequency measuring unit 164 can measure a ciliary beat frequency (CBF) included in a region of interest (ROI) using cross-correlation. The image processing unit 166 can express the cilia in the image data in various ways according to the range of the measured ciliated beat frequency. Detailed description of each component will be omitted since being repeated as described above.

Hereinafter, referring to FIGS. 2 to 6A and 6B, a method for measuring motility of ciliated cells in the respiratory tract by the processor 16 will be described. Here, the operations of the processor 16 may be performed in the apparatus 10.

Referring to FIG. 2, the processor 16 obtains image data having a plurality of frames of the respiratory tract organoids (S210).

As described above, the processor 16 acquires image data of the respiratory tract organoids from an external device (not shown), and analyzes the image data to measure motility of ciliary cells in the respiratory tract.

Here, the image data may include a plurality of frames. For example, the image data may include 300 frames. In this instance, when the number of frames per second of the image data is 300 fps (frames per second), the image data can be data of one second length.

Referring to FIG. 3, the processor 16 may capture images with the number of frames, for instance, 300 frames, based on the number of frames per second, for instance, 300 fps, from the obtained image data for the predetermined period of time, for instance, one second.

Once the image capturing is complete, the processor 16 can perform pre-processing through image enhancement and image registration with respect to the image data having the plurality of frames. This is to minimize motion artifacts that may occur during image recording by performing preprocessing and increase the quality of data to be used for analysis, thereby increasing accuracy in data analysis.

Referring to FIG. 2, the processor 16 may perform motion-contrast imaging of the image data to identify the position of the ciliated cells (S220).

Specifically, the processor 16 extracts dynamic signal components according to movement of ciliary cells among data components included in the acquired image data, and can identify the position of the ciliated cells based on the extracted dynamic signal component.

Referring to FIG. 3, when motion-contrast imaging is performed using a plurality of frames of time series, dynamic signal components can be extracted from specific parts of the entire area of the image data, and the specific parts are classified and displayed by a specific color, thereby identifying the position of the ciliated cells. Here, each position can be expressed in a different color according to the intensity of the dynamic signal. There are various motion-contrast generating methods, for example, methods using an absolute value of a difference of inter-frame signals, a cross-correlation of the inter-frame signals, a standard deviation of the inter-frame signals, a dispersion of the inter-frame signals, and an eigen value decomposition of the inter-frame signals.

Referring to FIG. 2, the processor 16 may select a region of interest (ROI) related to the position of the ciliary cells from a user (S230).

Here, the size and the number of the regions of interest can be set by the user.

Next, the processor 16 can measure a ciliary beat frequency (CBF) related to motility of cilia included in the region of interest using the cross-correlation between the plurality of frames with respect to the region of interest (S240).

In detail, the processor 16 can measure the ciliary beat frequency by digitizing image similarity between a reference frame among the plurality of frames and the remaining frames into a correlation coefficient. In this instance, an object to determine the image similarity is a portion corresponding to the region of interest, and the processor 16 extracts only a portion corresponding to the region of interest from the entire area of the frames, thereby determining image similarity between the frames.

For example, if the number of frames is three, a correlation coefficient can be calculated through image similarity between a first frame and a second frame using the first frame as a reference frame, and then, a correlation coefficient can be calculated through image similarity between the first frame and a third frame.

If a cilia motion is normal, the correlation coefficient obtained by digitizing the image similarity between the reference frame and the remaining frames can be in the form of a waveform vibrating at a predetermined cycle, as illustrated in the graph of FIG. 3.

Moreover, the processor 16 can calculate the number of peaks of the waveform as the ciliated beat frequency. Referring to the graph illustrated in FIG. 3, since the number of peaks of the waveform is 8, the ciliary beat frequency is calculated at 8 Hz.

Since the calculated ciliary beat frequency indicates movement of the ciliary cells in the region of interest, since cilia of one ciliated epithelium are moving at a relatively constant frequency, the calculated ciliary beat frequency can be considered as a ciliary beat frequency of an individual cilium.

Differently from the existing method using a frequency analysis of a pixel signal, the measuring method according to the present disclosure does not generate ambiguity in frequency analysis since being based on similarity between image patterns. In addition, the measuring method according to the present disclosure can reduce inconvenience of precisely adjusting the focus during an image record of ciliated cells since the image focus even if being somewhat blur does not significantly affect the determination of the ciliary beat frequency. A detailed description of the above will be provided hereinafter.

Referring to FIG. 2, the processor 16 can display the cilia included in the region of interest in a predetermined display method based on the range of the measured ciliary beat frequency (S250).

Here, the preset display method may include at least one of a color, an edge thickness, and a 3D depth value to be applied to the cilia included in the region of interest.

As an example, in a display method related to the color, the processor 16 identifies a color corresponding to the range of the measured ciliary beat frequency, and displays the cilia with the identified color. For example, if the ciliary beat frequency measured for the region of interest is 8 Hz and the color corresponding to 8 Hz is orange, the cilia included in the region of interest can be mapped and displayed to an orange color.

As another example, in a display method related to the edge thickness, the processor 16 identifies an edge thickness corresponding to the range of the measured ciliary beat frequency, and displays the edge of the cilia into the identified edge thickness.

As a further example, in a display method related to the 3D depth value, the image data includes left-eye and right-eye image data for 3D display of the cilia. The processor 16 can display the cilia in a 3D format using the left-eye and right-eye image data. The processor 16 identifies a 3D depth value corresponding to the range of the measured ciliary vibration frequency, and displays the cilia in 3D form by applying the identified 3D depth value.

As described above, the present disclosure can display the ciliary beat frequency of the cilia in the image data by the various display methods so that the user can quickly determine the range of the ciliary beat frequency in the image data through one of the display methods with the naked eye, thereby quickly predicting respiratory diseases associated with the range of the ciliary beat frequency.

Referring to FIG. 4, a method for measuring the motility of ciliary cells in the respiratory tract will be described.

If there are a number of regions of interest, that is, when a plurality of regions of interest are selected by the user in operation S230, the processor 16 can measure a ciliary beat frequency for each of regions of interest in operation S240.

In this instance, the size of the plurality of regions of interest can be varied according to the user's setting.

Specifically, in operation S230, the processor 16 can measure a ciliary beat frequency for each of the regions of interest.

For example, if the regions of interest are two, the processor 16 extracts only a portion corresponding to the first region of interest from the entire region of the frames and determines similarity between the frames to measure a ciliary beat frequency of the first region of interest. Thereafter, the processor 16 extracts only a portion corresponding to the second region of interest from the entire region of the frames and determines similarity between the frames to measure a ciliary beat frequency for the second region of interest.

In operation S240, the processor 16 can display each of the plurality of regions of interest in the display method corresponding to the range of each ciliary beat frequency measured for each of the regions of interest.

For example, in the case that the color-related display method is used, if the ciliary beat frequency for the first region of interest was measured at 6 Hz and the ciliary frequency for the second region of interest was measured at 7 Hz, the cilia included in the first region of interest is displayed in yellow-green which corresponds to 6 Hz, and the cilia included in the second region of interest is displayed in yellow which corresponds to 7 Hz.

Referring to FIG. 4, with respect to seven regions of interest, the cilia included in each of the seven regions of interest are displayed in different colors according to the range of the ciliary beat frequencies measured for the seven regions of interest.

As described above, the different ciliary beat frequencies can be automatically measured through repeated setting of the regions of interest. Finally, all the ciliary beat frequencies in the image can be displayed in a color map, so that the user can determine distribution of the ciliary beat frequencies of the ciliated cells arranged throughout the image at a glance, and it enables more quantitative and statistical analysis.

Referring to FIG. 5, in the case that a plurality of organoids in a microscope are observed, a method for measuring motility of ciliated cells in the respiratory tract will be described.

As illustrated in FIG. 5, if three organoids #1, #2 and #3 in the microscope were found, operations S210 to S240 are individually performed for each organoid. Accordingly, final result data, for instance, a color map, can be generated for each of the organoids #1, #2 and #3. Since the detailed description of the above is repeated as described above, it will be omitted.

Referring to FIGS. 6A and 6B, a method for measuring motility of ciliated cells in the respiratory tract is described in the case that there is a focus movement of the microscope.

Specifically, when focus movement occurs while the user observes the organoids through the microscope, the ciliary beat frequency measured using the image data before the focus movement and the ciliary beat frequency measured using the image data after the focus movement can be measured to be the same.

FIG. 6A shows results obtained by performing operations S220 and S240 for the image data before the focus movement. FIG. 6B shows results obtained by performing operations S220 and S240 for the image data after the focus movement that a focal point is moved 10 µm or more in a depth direction. In this instance, an analysis is performed using the same location in the two image data as the region of interest.

As illustrated in FIGS. 6A and 6B, the ciliary beat frequency before the focus movement and the ciliary beat frequency after the focus movement were measured equally at 7 Hz. In other words, even when the focus of the microscope is moved in the depth direction, the ciliary beat frequencies measured in the ciliary beat frequency measuring operation can be measured to be the same.

Although FIG. 2 shows a sequential execution of operations S210 to S250, it is just an exemplary embodiment of the technical idea of the present disclosure. Therefore, it is to be understood by those of ordinary skill in the art that various modifications and variations can be made without departing from the essential characteristics of the present disclosure, for instance, the sequential order illustrated in FIG. 2 may be changed or one or more operations of operations S210 to S250 may be executed in parallel. So, FIG. 2 is not limited to the time series sequence.

According to the present disclosure, provided is a new type of high-speed automated CBF measurement technology capable of completely solving the technical issue of the existing methods using motion-contrast imaging and the image correlation.

In detail, it is possible to accurately identify the position of ciliated cells of individual ciliated epithelium in a microscope image through the motion-contrast imaging. Therefore, the present disclosure can provide a guide map for accurate ROI setting to a user.

Furthermore, through the image correlation-based CBF analysis, the present disclosure can accurately evaluate ciliated cells of the individual ciliated epithelium without being affected by external noise and focus.

In addition, the present disclosure can easily interwork with a general biometric microscope, a medical microscope, and a high-resolution microscope, can perform CBF measurement in real time on the spot immediately after data collection, is easy to manipulate, and can perform CBF mapping for the entire imaging area, thereby being used for an animal experiment and a clinical study, and being used during and after surgery.

The method according to an embodiment of the present disclosure can be implemented as a program (or application) to be executed by being combined with a server which is hardware, and can be stored in a medium. Here, the computer may be the apparatus 10 described above.

The program may include code coded as a computer language, such as C, C++, Java, machine language, and high-level programming language, such as, matlab, labview, python, etc., which a processor (CPU) of the computer can read through a device interface of a computer. The code may include a functional code associated with a function defining necessary functions for executing the methods, and may include an execution procedure-related control code in which the processor of the computer needs to execute the functions according to predetermined procedures. In addition, the code may further include additional information necessary for the processor of the computer to execute the functions or memory reference-related code for whether the media should be referenced in which location (address) of the internal or external memory of the computer. Moreover, if communication with any other computer or server in a remote location is required to execute the functions by the process of the computer, the code may further include communication-related code for how to communicate with any other computer or server at a remote location using the communication module of the computer, or whether or not any information or media should be transmitted and received in the communication.

The method or algorithm described in relation to the embodiments of the present disclosure can be directly embodied in hardware, can be embodied in a software module executed by hardware, or can be embodied by combination thereof. The software module can reside in a random access memory (RAM), a read-only memory (ROM), an erasable programmable read-only memory (EPROM), an electrically erasable programmable read-only memory (EEPROM), a flash memory, a hard disk, a detachable disk, a CD-ROM, or a medium readable by a computer, well-known in the technical field to which the present disclosure belongs.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

The invention claimed is:

1. A method for measuring motility of ciliated cells in a respiratory tract, the method comprising:
   acquiring, through a microscope, first image data including a plurality of first frames of respiratory tract organoids;
   identifying positions of ciliated cells by performing motion-contrast imaging on the first image data;
   receiving a selection of a region of interest (ROI) related to the position of the ciliated cells;
   measuring a ciliary beat frequency (CBF) related to motility of cilia included in the selected ROI, using cross-correlation between the plurality of frames;
   expressing the cilia included in the ROI in a preset display method, based on a range of the measured CBF,
   wherein the measuring the CBF comprises digitizing image similarity between a reference frame among the plurality of frames and remaining frames into a correlation coefficient;
   acquiring, through the microscope, second image data, in which a focus is moved from the first image data, for a plurality of second frames of respiratory tract organoids;
   identifying positions of ciliated cells by performing motion-contrast imaging on the second image data;
   measuring the CBF related to motility of cilia included in the same ROI as the selected ROI, using cross-correlation between the plurality of second frames; and
   expressing the same cilia included in the same ROI in the preset display method, based on the range of the measured CBF.

2. The method according to claim 1, wherein the identifying the positions of ciliated cells comprises:
   extracting a dynamic signal component according to motions of the ciliary cells among data components included in the first image data; and
   identifying the positions of the ciliated cells based on the extracted dynamic signal component.

3. The method according to claim 1, wherein the measuring the CBF comprises:
   measuring the CBF of each ROI of a plurality of regions of interest, and
   wherein the expressing the cilia comprises:
   displaying a respective ROI of the plurality of regions of interest in a particular color corresponding to a respective range of a respective measured CBF.

4. The method according to claim 1, wherein the correlation coefficient has a waveform vibrating at a predetermined period.

5. The method according to claim 4, wherein the measuring the CBF comprises:
   calculating a number of peaks of the waveform in the CBF.

6. A non-transitory computer-readable recording medium combined with a computer, which is hardware, and storing a computer program for executing the method according to claim 1.

7. An apparatus for measuring motility of ciliated cells in a respiratory tract, the apparatus comprising:
   a communication unit;
   a memory; and
   a processor configured to:
   acquire, through a microscope, first image data including a plurality of first frames of respiratory tract organoids;
   identify positions of ciliated cells by performing motion-contrast imaging on the first image data;
   receive a selection of a region of interest (ROI) related to the position of the ciliated cells;
   measure a ciliary beat frequency (CBF) related to motility of cilia included in the selected ROI, using cross-correlation between the plurality of frames;
   express the cilia included in the ROI in a preset display method, based on a range of the measured CBF,
   wherein the processor measures the CBF by digitizing image similarity between a reference frame among the plurality of frames and remaining frames into a correlation coefficient;
   acquire, through the microscope, second image data, in which a focus is moved from the first image data, for a plurality of second frames of respiratory tract organoids;
   identify positions of ciliated cells by performing motion-contrast imaging on the second image data;
   measure the CBF related to motility of cilia included in the same ROI as the selected ROI, using cross-correlation between the plurality of second frames; and
   express the same cilia included in the same ROI in the preset display method, based on the range of the measured CBF.

8. The apparatus according to claim 7, wherein the processor is further configured to:
   extract a dynamic signal component according to motions of the ciliary cells among data components included in the first image data; and
   identify the positions the ciliated cells based on the extracted dynamic signal component.

9. The apparatus according to claim 7, wherein the processor is further configured to:

measure the CBF of each ROI of a plurality of regions of interest; and display a respective ROI of the plurality of regions of interest in a particular color corresponding to a respective range of a respective measured CBF.

10. The apparatus according to claim 7, wherein the correlation coefficient has a waveform vibrating at a predetermined period.

11. The apparatus according to claim 10, wherein the processor is further configured to:

calculate the number of peaks of the CBF.

12. The method according to claim 1, further comprising:

repeating, for each organoid of the respiratory tract organoids, the acquiring the first image data, the identifying the positions of ciliated cells, the receiving the selection of the ROI, the measuring the CBF; and displaying a color map for each organoid of the respiratory tract organoids, which expresses each cilia in a different color.

* * * * *